(12) United States Patent
Katagi et al.

(10) Patent No.: US 10,036,691 B2
(45) Date of Patent: Jul. 31, 2018

(54) SPECIMEN PROCESSOR

(71) Applicant: HITACHI ALOKA MEDICAL, LTD., Mitaka-shi, Tokyo (JP)

(72) Inventors: Hitomi Katagi, Mitaka (JP); Haruki Shimokawabe, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 531 days.

(21) Appl. No.: 14/390,305

(22) PCT Filed: Apr. 4, 2013

(86) PCT No.: PCT/JP2013/060306
§ 371 (c)(1),
(2) Date: Oct. 2, 2014

(87) PCT Pub. No.: WO2013/154018
PCT Pub. Date: Oct. 17, 2013

(65) Prior Publication Data
US 2015/0079663 A1  Mar. 19, 2015

(30) Foreign Application Priority Data
Apr. 12, 2012 (JP) ................................ 2012-090850

(51) Int. Cl.
*G01N 35/10* (2006.01)
*G01N 1/31* (2006.01)

(52) U.S. Cl.
CPC ........... *G01N 1/31* (2013.01); *G01N 35/1016* (2013.01); *G01N 2035/1025* (2013.01)

(58) Field of Classification Search
CPC ............ G01N 2035/1025; G01N 35/1016
See application file for complete search history.

(56) References Cited

U.S. PATENT DOCUMENTS 5,555,920 A * 9/1996 Godolphin ............ A61J 1/2089
141/130
2005/0205788 A1   9/2005 Itoh
(Continued)

FOREIGN PATENT DOCUMENTS

CN  101806806 A  8/2010
JP  60-185134 A  9/1985
(Continued)

OTHER PUBLICATIONS

Office Action dated Feb. 24, 2016, issued in counterpart Chinese application No. 201380019864.1, with English translation. (17 pages).

(Continued)

*Primary Examiner* — Jonathan M Hurst
(74) *Attorney, Agent, or Firm* — Westerman, Hattori, Daniel & Adrian, LLP

(57) ABSTRACT

A dispensing unit that sucks and discharges a blood specimen via a nozzle. A liquid level-measuring unit that measures the liquid level height. A serum volume-estimating unit that estimates the volume of the serum separated in the blood specimen, on the basis of the total blood volume, said total blood volume corresponding to the volume of the blood specimen and having been derived from the liquid level height, and a hematocrit value. A residual volume-estimating unit that calculates the volume of the serum remaining after suction, on the basis of the serum volume estimated by the serum volume-estimating unit and the volume of the serum that is going to be sucked by the dispensing unit. A controller that controls the suction procedure of the dispensing unit so that the estimated residual volume is not less than the desired volume of the serum to be left in the blood collection tube.

9 Claims, 5 Drawing Sheets

(56) References Cited

U.S. PATENT DOCUMENTS

| | | |
|---|---|---|
| 2009/0191095 A1 | 7/2009 | Nakamura |
| 2009/0211380 A1 | 8/2009 | Tajima et al. |
| 2010/0210019 A1 | 8/2010 | Kurono et al. |
| 2013/0111978 A1 | 5/2013 | Mizumoto et al. |

FOREIGN PATENT DOCUMENTS

| | | |
|---|---|---|
| JP | 63-122959 A | 5/1988 |
| JP | 3-37568 A | 2/1991 |
| JP | 6-265554 A | 9/1994 |
| JP | 6-87870 U | 12/1994 |
| JP | 10-19900 A | 1/1998 |
| JP | 10-246727 A | 9/1998 |
| JP | 11-94840 A | 4/1999 |
| JP | 11-118809 A | 4/1999 |
| JP | 2001-337093 A | 12/2001 |
| JP | 2005-17219 A | 1/2005 |
| JP | 2005-17245 A | 1/2005 |
| JP | 2005-265813 A | 9/2005 |
| JP | 3120179 U | 3/2006 |
| JP | 2009-180607 A | 8/2009 |
| JP | 2012-18126 A | 1/2012 |
| WO | 2006/123771 A1 | 11/2006 |
| WO | 2012/002524 A1 | 1/2012 |

OTHER PUBLICATIONS

Office Action dated Jun. 23, 2015, issued in counterpart Chinese application No. 201380019864.1, with English translation. (19 pages).

Notification of Transmittal of Copies of Translation of the International Preliminary Report on Patentability (Chapter I or Chapter II) (Forms PCT/IB/338) of the International Application No. PCT/JP2013/060306 dated Oct. 16, 2014 with form PCT/IPEA/409.

Notice of Grounds for Rejection dated May 7, 2013 issued in corresponding application No. JP2012090850; English Tranlation (5 pages).

Notice of Grounds for Rejection dated Jun. 25, 2013 issued in corresponding application No. JP2012090850; English Tranlation (5 pages).

International Preliminary Report on Patentablility dated May 14, 2013 issued in corresponding application No. PCT/JP2013/060306; Partial Translation.

International Search Report dated May 14, 2013 issued in corresponding application No. PCT/JP2013/060306.

* cited by examiner

| SPECIMEN ID | SERUM QUANTITY | ESTIMATED REMAINING QUANTITY | BLOOD COLLECTION TUBE NUMBER | DISPENSED QUANTITY | DISCHARGED QUANTITY | DISPENSE RESULT |
|---|---|---|---|---|---|---|
| 0001 | 2800 | 2000 | 8 | 800 | 800 | NORMAL |
| 0002 | 3000 | 1000 | 8 | 2000 | 2000 | NORMAL |
| 0003 | 500 | 500 | 8 | — | — | DISPENSE DISCONTINUED |
| ... | ... | ... | ... | ... | ... | ... |

FIG. 5

SPECIMEN PROCESSOR

TECHNICAL FIELD

The present invention relates to a specimen processing device for processing a blood specimen.

BACKGROUND ART

When centrifugation processing is performed on a blood collection tube containing a blood specimen and a separating agent, the blood specimen becomes separated inside the blood collection tube into blood serum and blood clotting factor located on respective sides of the separating agent. For example, centrifugal force is applied in the direction toward the bottom of the blood collection tube, which results in the blood clotting factor, separating agent, and serum being separated from each other inside the blood collection tube and present in that order from the bottom. Subsequently, from inside the blood collection tube after being subjected to centrifugation, the serum is removed using a dispensing device or the like, and testing and analysis are performed on the serum remaining inside the blood collection tube and the serum removed from the blood collection tube.

For the testing and analysis of the serum remaining inside the blood collection tube, the serum must remain in a quantity required for the testing and analysis. However, although the quantity of serum removed from the blood collection tube can be relatively easily determined based on the suction volume of the dispensing device or the like, determining the remaining quantity of serum inside the blood collection tube is not easy.

For example, Patent Document 1 discloses a technique for detecting the separation position of the serum separated inside a test tube. If the serum separation position can be detected, the quantity of serum can be calculated based on the serum separation position, data on the shape of the test tube, and the like, for example. However, detection of the separation position is not easy and requires a complex detection device and the like.

Meanwhile, a hematocrit value, which indicates a ratio of volume occupied by blood cells in blood, is known as a medical numerical value. Patent Document 2 discloses a technique of using the hematocrit value to estimate the interface position (separation position) in a separated blood specimen.

PRIOR ART LITERATURE

Patent Documents

Patent Document 1: JP 2005-265813 A
Patent Document 2: JP H10-246727 A

SUMMARY OF THE INVENTION

Problems to be Solved by the Invention

Taking into consideration the above-described background art, the present inventors have made continuous efforts in research and development of a device for removing serum from inside a specimen container such as a blood collection tube. In particular, the present inventors have focused on the technique for determining the remaining quantity of serum in a specimen container.

The present invention was created in the course of such research and development. An object of the present invention is to provide a device for removing serum from inside a specimen container while allowing the serum amounting to a target remaining quantity to remain inside the specimen container.

Means for Solving the Problems

A preferred specimen processing device achieving the above-noted object comprises: a liquid level measuring unit that measures a liquid level height of a blood specimen placed inside a specimen container; a serum quantity estimating unit that estimates a quantity of serum separated in the blood specimen, based on a blood specimen quantity derived from the measured liquid level height and also based on a hematocrit value; a specimen suction unit that carries out suction and removal of the serum from inside the specimen container; a remaining quantity estimating unit that obtains an estimated remaining quantity of serum after suction, based on the serum quantity estimated by the serum quantity estimating unit and a serum suction quantity by which suction is to be performed by the specimen suction unit; and a control unit that controls a suction operation of the specimen suction unit in such a manner that the estimated remaining quantity does not become less than a target remaining quantity of serum that should remain inside the specimen container.

In the above-described configuration, a specific example of the specimen container is a blood collection tube. For example, by performing centrifugation processing using a centrifugation device on a blood collection tube containing a blood specimen and a separating agent, the blood specimen becomes separated inside the blood collection tube into blood serum and blood clotting factor located on respective sides of the separating agent. For example, the above-described specimen processing device processes a blood specimen inside a blood collection tube (specimen container) that has been subjected to centrifugation processing by a centrifugation device.

According to the above-described configuration, it is possible to remove serum from a specimen container while allowing the serum amounting to a target remaining quantity to remain inside the specimen container. Furthermore, it is possible to remove as much serum as possible insofar as the estimated remaining quantity of serum does not become less than the target remaining quantity.

In a desirable specific example, the specimen processing device further comprises a specimen information acquiring unit that acquires specimen information of the blood specimen placed inside the specimen container, and, when the specimen information of the blood specimen includes an individual hematocrit value for that blood specimen, the serum quantity estimating unit uses the individual hematocrit value to estimate the serum quantity of the blood specimen.

In a desirable specific example, when the specimen information of the blood specimen does not include the individual hematocrit value but includes a sex identification code for that blood specimen, the serum quantity estimating unit uses a male hematocrit value or a female hematocrit value in accordance with the sex identification code to estimate the serum quantity of the blood specimen.

In a desirable specific example, when the specimen information of the blood specimen includes neither the individual hematocrit value nor the sex identification code, the serum quantity estimating unit uses a male hematocrit value to estimate the serum quantity of the blood specimen.

In a desirable specific example, the specimen processing device further comprises a container information storing unit which receives registration of a correspondence relationship between a sample liquid level height, which is obtained when a sample is placed in the specimen container in a known quantity, and the known quantity, and the serum quantity estimating unit uses a conversion formula, which is obtained from the correspondence relationship, to derive the blood specimen quantity from the liquid level height of the blood specimen placed inside the specimen container.

In a desirable specific example, based on the serum quantity estimated by the serum quantity estimating unit and a serum suction quantity for each instance of suction among a plurality of instances of suction to be performed by the specimen suction unit, the remaining quantity estimating unit calculates an estimated remaining quantity of serum after suction concerning each instance of suction. Further, the control unit compares, for each instance of suction, the estimated remaining quantity after suction to the target remaining quantity, and when the estimated remaining quantity after suction is less than the target remaining quantity, the control unit performs control so that the specimen suction unit does not carry out the suction operation for that instance.

Advantages of the Invention

The present invention provides a device for removing serum from a specimen container while allowing the serum to remain inside the specimen container in a target remaining quantity.

BRIEF DESCRIPTION OF THE DRAWINGS

FIG. 5 is a diagram showing a specific example of results of processing by the specimen processing device of FIG. 1.

EMBODIMENTS OF THE INVENTION

Figure 1:
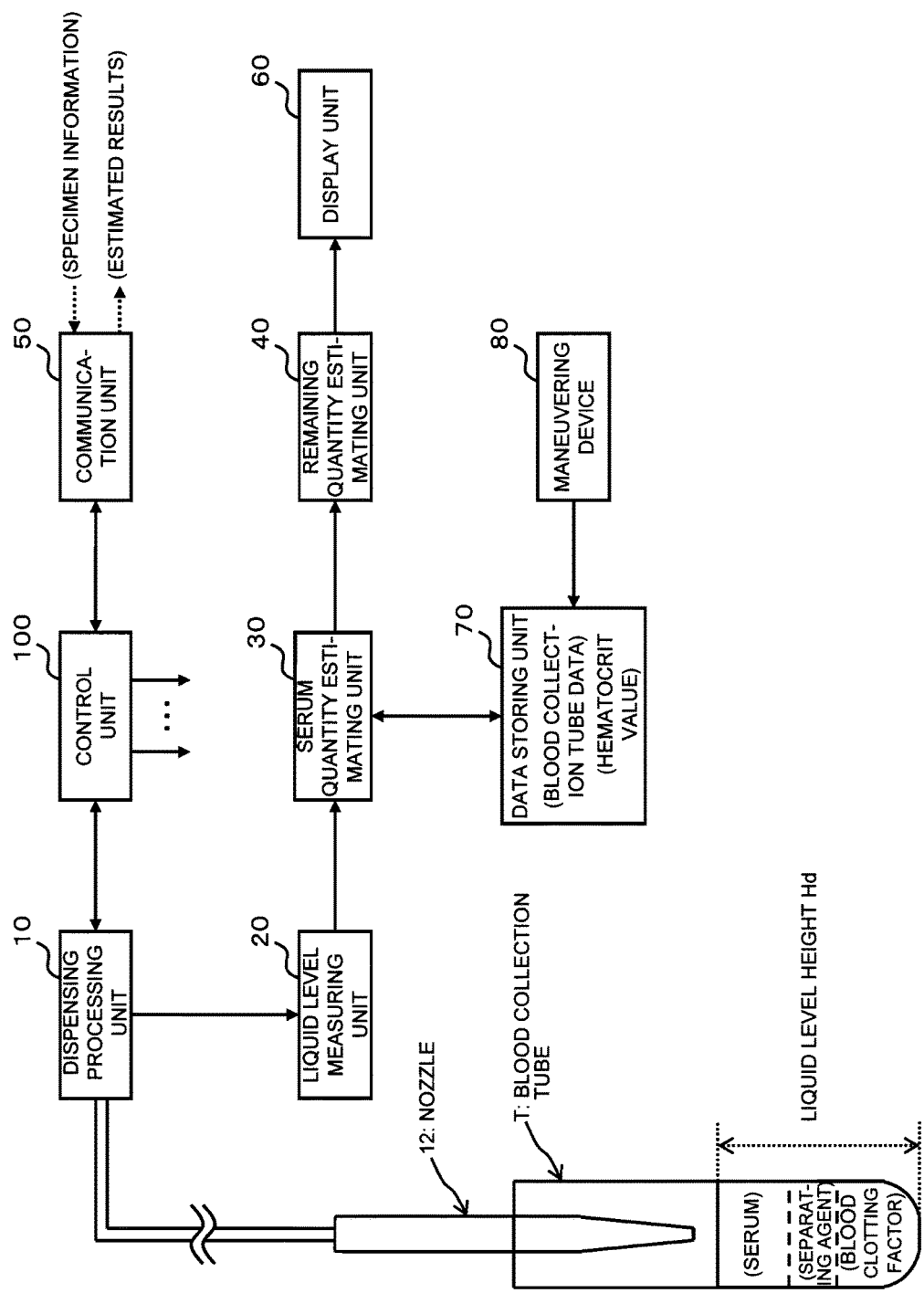
FIG. 1 is a diagram showing an overall configuration of a preferred specimen processing device for practicing the present invention.

FIG. 1 is a diagram showing an overall configuration of a preferred specimen processing device for practicing the present invention ("the present specimen processing device"). The present specimen processing device has a dispensing processing function, which comprises carrying out suction of a blood specimen placed in a blood collection tube T and discharging the blood specimen into a sub-specimen container. In a processing stage upstream of the present specimen processing device, the blood specimen inside the blood collection tube T is subjected to a centrifugation processing by a centrifugation device, for example, so that the blood specimen is separated inside the blood collection tube T into blood clotting factor, separating agent, and serum, located in that order from the bottom. From inside the blood collection tube T after being subjected to centrifugation, the serum is removed by means of the dispensing processing function of the present specimen processing device. The serum remaining inside the blood collection tube T and the serum removed from the blood collection tube T are forwarded to a processing stage downstream of the present specimen processing device and employed for testing and analysis.

A dispensing processing unit 10 comprises elements such as a nozzle drive mechanism for moving a nozzle 12, and a pump for drawing and discharging a blood specimen via the nozzle 12. For example, when a blood collection tube T received in a rack is transported to a dispensing position by a transport mechanism, the nozzle 12 is inserted into the blood collection tube T by the nozzle drive mechanism, and serum inside the blood collection tube T is drawn into the nozzle 12 by the pump. Subsequently, the nozzle 12 having the serum drawn inside is moved to a position of a sub-specimen container by the nozzle drive mechanism, and the serum is discharged into the sub-specimen container.

A liquid level measuring unit 20 measures the liquid level height Hd of the blood specimen placed inside the blood collection tube T. The liquid level measuring unit 20 detects the liquid level position and thereby measures the height Hd, which is the distance from a known position of the bottom of the blood collection tube T to the liquid level position. For the detection of the liquid level position, a pressure method is used, for example. That is, the tip of the nozzle 12 is moved gradually closer to the liquid level while air is being discharged from the tip, and the liquid level position is identified from a change in the air pressure that is caused immediately before the tip of the nozzle 12 contacts the liquid level or at the instant that the tip of the nozzle 12 contacts the liquid level. Instead of the pressure method, other known methods such as an optical sensor method, a microwave method, and an electrostatic method may be used to detect the liquid level position.

A serum quantity estimating unit 30 derives the quantity of the blood specimen; namely, the total blood quantity Vd, from the measured liquid level height Hd. Further, based on the total blood quantity Vd and a hematocrit value, the serum quantity estimating unit 30 estimates the quantity of the serum separated in the blood specimen. The hematocrit value is a value indicating a ratio of volume occupied by blood cells in blood. The estimated serum quantity Vm is calculated from the total blood quantity Vd and the hematocrit value according to the following formula.

Estimated serum quantity $Vm$=total blood quantity $Vd \times (100 - \text{hematocrit value})$     [Numerical Formula 1]

When deriving the total blood quantity Vd from the liquid level height Hd, blood collection tube data stored in a data storing unit 70 are employed. The blood collection tube data are registered in the data storing unit 70 in advance, prior to the dispensing processing by the present specimen processing device.

Figure 2:
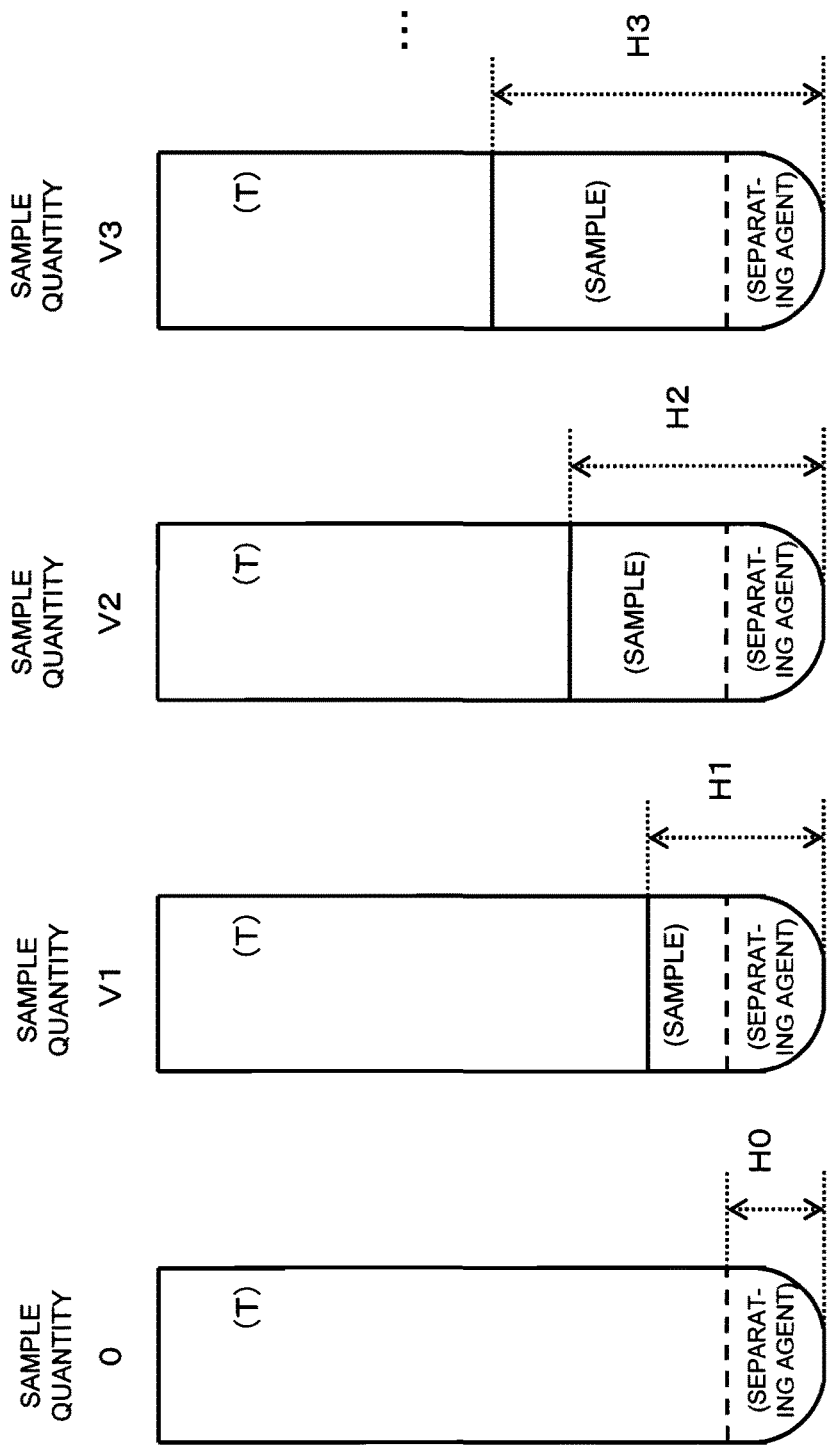
FIG. 2. is a diagram for explaining registration of blood collection tube data.

FIG. 2 is a diagram for explaining the registration of the blood collection tube data. Blood collection tubes T have shapes and the like that are varied for each provider (for example, manufacturer) of the blood collection tubes T. Further, blood collection tubes T for centrifugation use are generally provided to the user (testing party) with a known quantity of separating agent placed therein in advance by the provider. Accordingly, in the present specimen processing device, it is assumed that blood collection tubes T that are identical in shape, size, and amount of separating agent belong to the same type, and the blood collection tube data are registered for each of the respective types (for example, for each provider).

FIG. 2 shows an example registration of blood collection tube data concerning one certain type of blood collection tube T. In other words, the plurality of blood collection tubes T shown in FIG. 2 are identical to each other in shape, size, and amount of separating agent. Naturally, all of the plurality of blood collection tubes T shown in FIG. 2 may be the same blood collection tube T.

When registering blood collection tube data, known quantities of a sample are placed in the blood collection tube T, and the liquid level height of the sample is measured for each of the known quantities. The sample may be blood or other liquid such as water.

FIG. 2 shows a plurality of states obtained when the sample is place in the same blood collection tube T in the known quantities of 0, V1, V2, V3, etc. For example, the liquid level height is H1 when the sample quantity is V1, the liquid level height is H2 when the sample quantity is V2, and the liquid level height is H3 when the sample quantity is V3. When the sample quantity is 0 (zero), the height H0 of the separating agent is measured. Subsequently, the blood collection tube data indicating the correlations between the known sample quantities and their respective liquid level heights are registered.

Furthermore, based on the correlation relationship between the known sample quantities and the liquid level heights, an approximation formula for deriving a sample quantity from a liquid level height is created. More specifically, the following approximation formula for obtaining the blood specimen quantity (total blood quantity) Vd from the liquid level height Hd of the blood specimen is created.

$$Vd = \alpha \times Hd + \beta \quad \text{[Numerical Formula 2]}$$

$\alpha$ and $\beta$ in Numerical Formula 2 are determined based on the correlation relationship between the known sample quantities and the liquid level heights. It is alternatively possible to create an approximation formula containing Hd in the form of a quadratic or higher-order term. The approximation formula created as such is also registered as the blood collection tube data. In this way, the blood collection tube data are registered for each type of blood collection tube T.

Referring again to FIG. 1, from the liquid level height Hd measured by the liquid level measuring unit 20, the serum quantity estimating unit 30 derives the blood specimen quantity; namely, the total blood quantity Vd, using, for example, the approximation formula of Numerical Formula 2 stored in the data storing unit 70. Further, based on the total blood quantity Vd and the hematocrit value, the serum quantity estimating unit 30 estimates the serum quantity inside the blood collection tube T using Numerical Formula 1.

In the data storing unit 70, a male hematocrit value Htm and a female hematocrit value Htf are also registered prior to the dispensing processing. A hematocrit value of a male person is approximately 42 to 45 percent, while a hematocrit value of a female person is approximately 38 to 42 percent. Accordingly, for example, any values selected from within these respective numerical ranges are registered as the male hematocrit value Htm and the female hematocrit value Htf, respectively.

For example, it may be configured such that the data storing unit 70 has stored therein the mean value of the range from 42 to 45 percent as the default male hematocrit value Htm and the mean value of the range from 38 to 42 percent as the default female hematocrit value Htf, and, according to necessity, the user (testing party) can change the setting of the male hematocrit value Htm and the female hematocrit value Htf using a maneuvering device 80.

A remaining quantity estimating unit 40 calculates an estimated remaining quantity of serum after suction, based on the serum quantity estimated by the serum quantity estimating unit 30 and a serum suction quantity by which suction is going to be performed by the dispensing processing unit 10. The suction quantity by which suction is going to be performed by the dispensing processing unit 10 is communicated from a control unit 100 to the remaining quantity estimating unit 40, for example. Further, the estimated remaining quantity calculated by the remaining quantity estimating unit 40 is communicated to the control unit 100.

The control unit 100 controls a suction operation of the dispensing processing unit 10 in such a manner that the estimated remaining quantity does not become less than a target remaining quantity of serum that should remain inside the blood collection tube T. In other words, the control unit 100 performs the control so that the serum remains inside the blood collection tube T in the target remaining quantity.

The present specimen processing device forms, together with the devices in charge of the upstream and downstream processing stages such as devices related to centrifugation and testing and analysis, a system in which these devices are mutually associated. This system as a whole is managed by a host computer. The present specimen processing device exchanges information with the host computer via a communication unit 50.

The communication unit 50 acquires, from the host computer, specimen information concerning the blood specimen that is inside the blood collection tube T and is to be subjected to the dispensing processing by the present specimen processing device. The specimen information includes a necessary serum remaining quantity Vs, which is a remaining quantity of serum that should be remaining in the blood collection tube T after the dispensing processing. The control unit 100 sets this necessary serum remaining quantity Vs as the target remaining quantity of serum that should be left inside the blood collection tube T.

The specimen information of the blood specimen may further include an individual hematocrit value that has been obtained individually for this blood specimen, and a sex identification code indicating whether this blood specimen was obtained from a male or female person. The communication unit 50 transmits, to the host computer, estimated results such as the serum quantity estimated by the serum quantity estimating unit 30 and the estimated remaining quantity calculated by the remaining quantity estimating unit 40.

The control unit 100 refers to information such as the specimen information acquired by the communication unit 50, and controls the present specimen processing device as a whole. Further, information such as the serum quantity calculated by the serum quantity estimating unit 30, the estimated remaining quantity calculated by the remaining quantity estimating unit 40, and a result of the dispensing processing by the present specimen processing device are displayed on a display unit 60.

Below, specimen processing performed using the present specimen processing device is further described in detail. In the following description, elements already shown in FIG. 1 are referred to using the same reference symbols used in FIG. 1.

Figure 3:
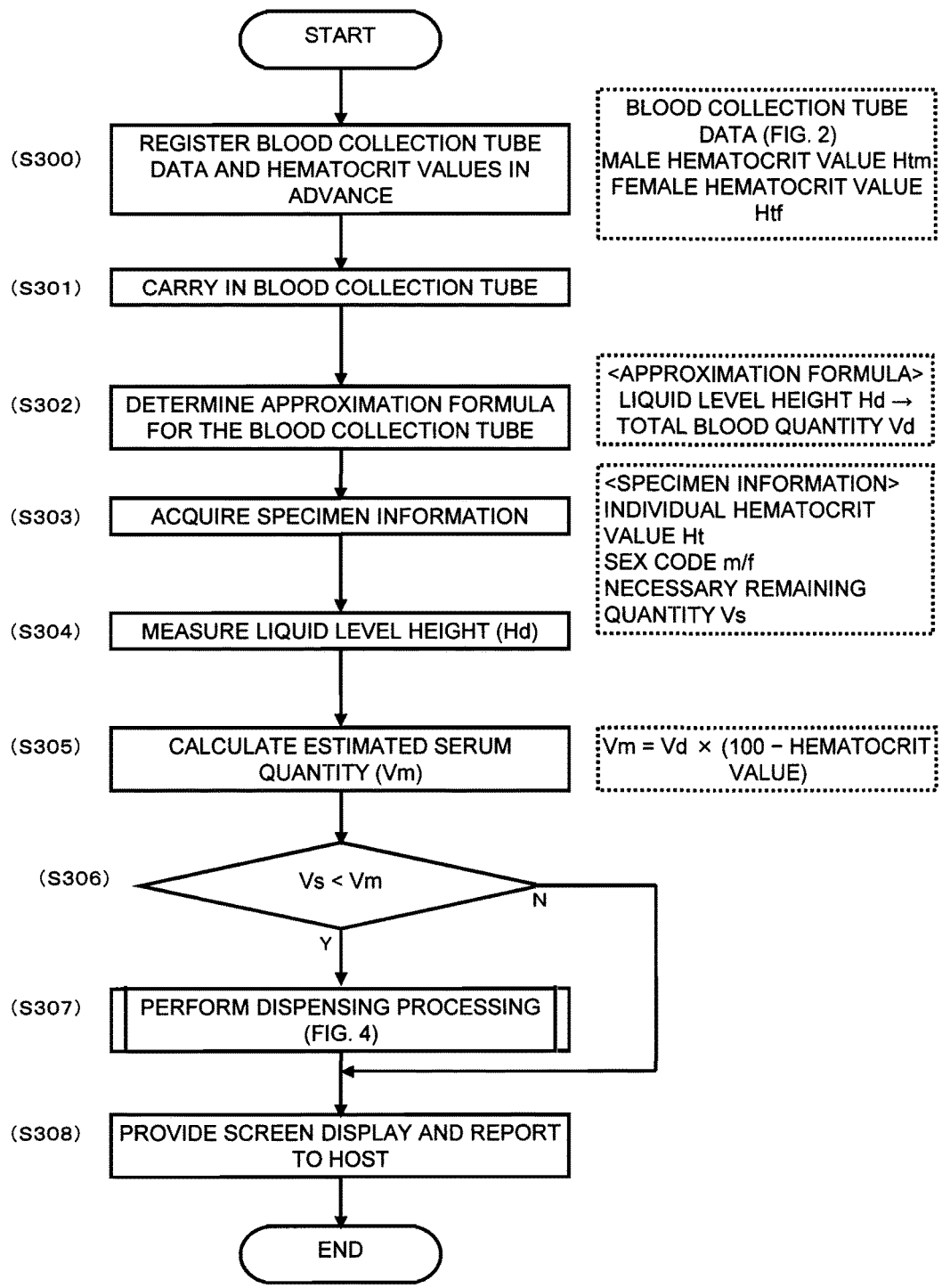
FIG. 3. is a flowchart showing an entire flow of specimen processing performed by the specimen processing device of FIG. 1.

FIG. 3 is a flowchart showing an entire flow of specimen processing performed by the specimen processing device of FIG. 1. First, the blood collection tube data and the hematocrit values are registered in advance in the data storing unit 70 (S300). The blood collection tube data are as detailed above with reference to FIG. 2. Also, as explained above, the male hematocrit value Htm and the female hematocrit value Htf may be registered as the hematocrit values.

Next, a blood collection tube T containing a blood specimen that has been subjected to centrifugation processing by a centrifugation device in an upstream processing stage, for example, is transported into the present specimen processing device and positioned at the dispensing position (S301), and the approximation formula for this blood collection tube T is determined (S302). In other words, the serum quantity estimating unit 30 acquires the approximation formula of Numerical Formula 2, for example, that is stored in the data storing unit 70.

Further, specimen information concerning the blood specimen inside the blood collection tube T positioned at the dispensing position is acquired from the host computer via the communication unit 50 (S303). The specimen information includes a necessary serum remaining quantity Vs, and may further include an individual hematocrit value Ht and a sex identification code.

Subsequently, the liquid level measuring unit 20 measures a liquid level height Hd inside the blood collection tube T positioned at the dispensing position (S304). Then, the serum quantity estimating unit 30 derives a total blood quantity Vd from the liquid level height Hd using the approximation formula, and further, based on the total blood quantity Vd and the hematocrit value and using Numerical Formula 1, the serum quantity estimating unit 30 calculates an estimated serum quantity Vm inside the blood collection tube T (S305).

When performing this calculation, if the specimen information of the blood specimen includes an individual hematocrit value Ht for that blood specimen, the serum quantity estimating unit 30 uses the individual hematocrit value Ht to calculate the serum quantity Vm. Further, if the specimen information of the blood specimen does not include the individual hematocrit value Ht but includes a sex identification code for that blood specimen, the serum quantity estimating unit 30 uses the male hematocrit value Htm or the female hematocrit value Htf in accordance with the sex identification code to calculate the serum quantity Vm. In other words, the male hematocrit value Htm is used when the blood specimen was obtained from a male person, and the female hematocrit value Htf is used when the blood specimen was obtained from a female person.

Furthermore, if the specimen information of the blood specimen includes neither the individual hematocrit value Ht nor the sex identification code, the serum quantity estimating unit 30 uses the male hematocrit value Htm to calculate the serum quantity Vm. As the male hematocrit value Htm is greater than the female hematocrit value Htf, the serum quantity Vm calculated according to Numerical Formula 1 becomes smaller when the male hematocrit value Htm is used. Accordingly, when both of the individual hematocrit value Ht and the sex are unknown, the male hematocrit value Htm is used to estimate a small serum quantity Vm, so that a remaining quantity can be ensured more reliably.

After the serum quantity Vm inside the blood collection tube T is calculated by the serum quantity estimating unit 30, the control unit 100 compares the necessary serum remaining quantity Vs and the serum quantity Vm with each other (S306). If the serum quantity Vm is greater than the necessary serum remaining quantity Vs, the dispensing processing is carried out (S307). In addition, the result of the dispensing processing is displayed on the display unit 60, and the result of the dispensing processing is also reported to the host computer from the communication unit 50 (S308). On the other hand, if it is found in step S306 that the serum quantity Vm is less than or equal to the necessary serum remaining quantity Vs, the dispensing processing is not carried out. In addition, a warning screen or the like indicating that the dispensing processing was not carried out is displayed, and also a report indicating that the dispensing processing was not carried out is provided to the host computer from the communication unit 50 (S308).

Figure 4:
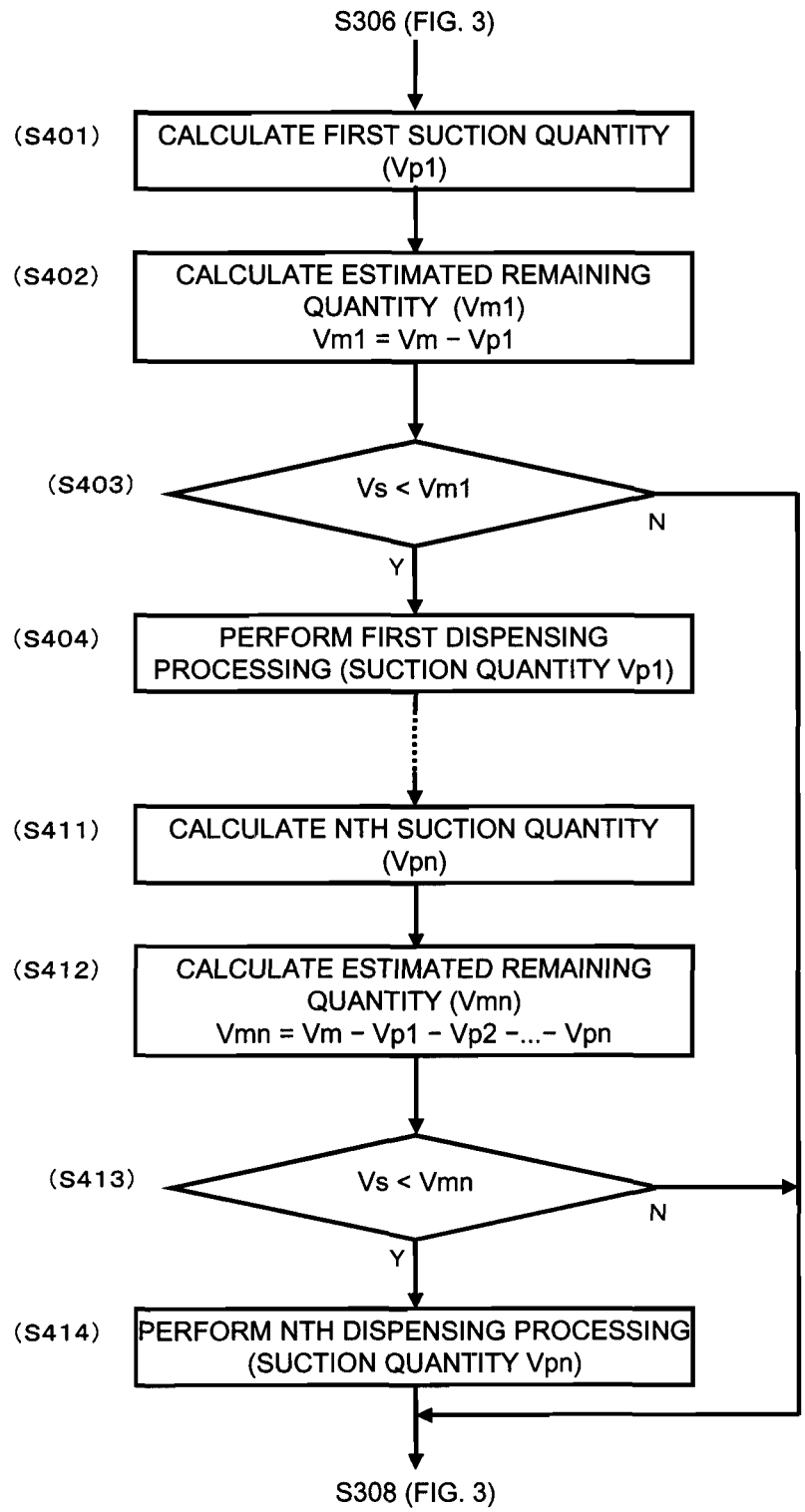
FIG. 4 is a flowchart showing a dispensing processing performed by the specimen processing device of FIG. 1.

FIG. 4 is a flowchart showing the dispensing processing performed by the specimen processing device of FIG. 1. That is, the flowchart of FIG. 4 shows the dispensing processing carried out in step S307 of FIG. 3. In this dispensing processing, serum is removed from the blood collection tube T over a plurality of instances. First, the control unit 100 calculates a first suction quantity Vp1 (S401). For example, the first suction quantity Vp1 is calculated based on information such as dispensing processing instruction information acquired from the host computer via the communication unit 50, or dispensing processing instruction information input by the user via the maneuvering device 80.

After the suction quantity Vp1 is calculated, the remaining quantity estimating unit 40 calculates an estimated remaining quantity of serum after first suction; i.e., Vm1=Vm−Vp1 (S402). When the estimated remaining quantity Vm1 is calculated, the control unit 100 compares the necessary serum remaining quantity Vs and the estimated remaining quantity Vm1 with each other (S403). If the estimated remaining quantity Vm1 is greater than the necessary serum remaining quantity Vs, it is judged that the necessary remaining quantity Vs of serum can be retained after the first instance of dispensing processing (first suction), and the control unit 100 controls the dispensing processing unit 10 to carry out the first instance of dispensing processing (S404).

On the other hand, if the estimated remaining quantity Vm1 is less than or equal to the necessary serum remaining quantity Vs in step S403, the first instance of dispensing processing is not carried out, and the procedure proceeds to step S308 of FIG. 3, in which a warning screen or the like indicating that the first instance of dispensing processing was not carried out is displayed, and also a report indicating that the dispensing could not be performed is provided to the host computer from the communication unit 50.

For each instance of suction, the control unit 100 compares the estimated remaining quantity after suction to the necessary serum remaining quantity Vs, and, when the estimated remaining quantity after suction is less than or equal to the necessary serum remaining quantity Vs, the controller performs control so that the dispensing processing unit 10 does not carry out the dispensing processing for that instance. More specifically, for the nth instance of dispensing processing, the control unit 100 calculates the nth suction quantity Vpn (S411), the remaining quantity estimating unit 40 calculates the nth estimated serum remaining quantity, i.e., Vmn=Vm−Vp1−Vp2− . . . −Vpn (S412), and the control unit 100 compares the necessary serum remaining quantity Vs and the estimated remaining quantity Vmn with each other (S413).

Here, if the estimated remaining quantity Vmn is greater than the necessary serum remaining quantity Vs, it is judged that the necessary remaining quantity Vs of serum can be retained after the nth instance of dispensing processing, and the control unit 100 controls the dispensing processing unit 10 to carry out the nth instance of dispensing processing (S414). If the nth instance of dispensing processing is the last instance, the procedure proceeds to step S308 of FIG. 3, in which the result of the dispensing processing is displayed on the display unit 60, and the result of the dispensing processing is also reported to the host computer from the communication unit 50.

On the other hand, if the estimated remaining quantity Vmn is less than or equal to the necessary serum remaining quantity Vs in step S413, the nth instance of dispensing processing is not carried out, and the procedure proceeds to step S308 of FIG. 3, in which a warning screen or the like indicating that the nth instance of dispensing processing was not carried out is displayed, and also a report indicating that the nth instance of dispensing was not performed is provided to the host computer from the communication unit 50.

FIG. 5 is a diagram showing a specific example of results of processing by the specimen processing device of FIG. 1. For example, the content shown in FIG. 5 is displayed on the display unit 60 as a reporting screen. Also, information indicating the content shown in FIG. 5 is transmitted from the communication unit 50 to the host computer.

A specimen ID is an identifier assigned individually to each blood specimen. For each blood specimen, the serum quantity calculated by the serum quantity estimating unit 30 and the estimated remaining quantity calculated by the remaining quantity estimating unit 40 are indicated in numerical values. A blood collection tube number denotes the type of the blood collection tube that contained each blood specimen. In addition, for each blood specimen, a dispensed quantity (quantity subjected to suction), a discharged quantity that was discharged into a sub-specimen, and the like are indicated in numerical values.

Further, for each blood specimen, a dispense result is indicated. In the example of FIG. 5, it is indicated that the dispensing processing was carried out normally for the blood specimens labeled with specimen ID 0001 and specimen ID 0002, and that the dispensing processing was not carried out (was discontinued) for the blood specimen labeled with specimen ID 0003. Alternatively, a dispense result may be configured to indicate, for each instance among the plurality of instances of dispense processing, a dispensed quantity, estimated remaining quantity, and judgment concerning whether the result was normal or abnormal.

A preferred embodiment of the present invention has been described above. According to the above-described embodiment, since as much serum as possible can be removed from a blood collection tube while allowing the serum amounting to the necessary serum remaining quantity Vs to remain inside the blood collection tube, it is possible to make an effective use of the serum. Further, because whether or not to execute a dispensing processing is determined by comparing the necessary serum remaining quantity and the estimated serum quantity with each other, execution of the dispensing processing can be avoided when the quantity of serum is not sufficient, for example. Furthermore, as the dispensing processing is carried out while checking the estimated remaining quantity, malfunction of the nozzle 12 that may be caused by absorbing the separating agent can also be avoided, for example. Moreover, it is possible to keep, as a record of evidence, information such as the serum quantity before the dispensing processing and the estimated remaining quantity after the dispensing processing.

LIST OF REFERENCE SYMBOLS 10 dispensing processing unit, 20 liquid level measuring unit, 30 serum quantity estimating unit, 40 remaining quantity estimating unit, 50 communication unit, 60 display unit, 70 data storing unit, 80 maneuvering device, 100 control unit.

The invention claimed is:

1. A method for processing a specimen using a specimen processing device comprising a specimen suction unit, the specimen suction unit being configured to carry out suction and removal of serum from inside a specimen container, the serum having been separated in a blood specimen placed inside the specimen container, the method comprising:
measuring a liquid level height of the blood specimen;
estimating a quantity of the serum separated in the blood specimen, based on (i) a blood specimen quantity derived from the measured liquid level height and (ii) a hematocrit value, the hematocrit value being an individual hematocrit value corresponding to an individual from whom the blood specimen is obtained, a male hematocrit value, or a female hematocrit value;
estimating a remaining quantity of serum to remain in the specimen container after suction, based on the estimated quantity of serum and a quantity of serum to be suctioned from side the specimen container;
controlling a suction operation of the specimen suction unit in such a manner that the estimated remaining quantity does not become less than a target remaining quantity of serum that should remain inside the specimen container;
storing specimen container data for use in obtaining the blood specimen quantity from the liquid level height of the blood specimen placed inside the specimen container; and
acquiring specimen information of the blood specimen, wherein
assuming that specimen containers that are identical in shape, size, and amount of separating agent belong to a same type, the method further comprises storing specimen container data for each type, and deriving the blood specimen quantity from the liquid level height of the blood specimen placed inside the specimen container, according to the specimen container data corresponding to the specimen container, and
when the specimen information of the blood specimen does not include the individual hematocrit value but includes a sex identification code for that blood specimen, the method further comprises estimating the serum quantity of the blood specimen based on a male hematocrit value or a female hematocrit value in accordance with the sex identification code.

2. The method according to claim 1, wherein the method comprises controlling the suction operation of the specimen suction unit so that the serum remains inside the specimen container in the target remaining quantity.

3. The method according to claim 1, wherein, when the estimated remaining quantity is less than the target remaining quantity, the method comprises controlling the specimen suction unit so that the specimen suction unit does not perform suction operation.

4. The method according to claim 1, wherein when the specimen information of the blood specimen includes an individual hematocrit value for that blood specimen, the method comprises estimating the serum quantity of the blood specimen based on the individual hematocrit value.

5. The method according to claim 1, wherein when the specimen information of the blood specimen includes neither the individual hematocrit value nor the sex identification code, the method comprises estimating the serum quantity of the blood specimen based on a male hematocrit value.

6. The method according to claim 4, wherein, when the specimen information of the blood specimen includes neither the individual hematocrit value nor the sex identification code, the method comprises estimating the serum quantity of the blood specimen based on a male hematocrit value.

7. The method according to claim 1, wherein the specimen container data includes a correspondence relationship between a sample liquid level height, which is obtained when a sample is placed in the specimen container in a known quantity, and the known quantity, and the method comprises deriving the blood specimen quantity from the liquid level height of the blood specimen placed inside the specimen container based on a conversion formula obtained from the correspondence relationship.

8. The method according to claim 1, wherein the method comprises calculating an estimated remaining quantity of serum after suction concerning each instance of suction based on the estimated serum quantity estimated and a serum suction quantity for each instance of suction among a plurality of instances of suction to be performed by the specimen suction unit, and comparing, for each instance of suction, the estimated remaining quantity after suction to the target remaining quantity, and when the estimated remaining quantity after suction is less than the target remaining quantity, controlling the specimen suction unit so that the specimen suction unit does not perform the suction operation for that instance.

9. The method according to claim 1, wherein the method comprises setting a necessary serum remaining quantity included in the specimen information of the blood specimen as the target remaining quantity.

* * * * *